(12) United States Patent
Perry

(10) Patent No.: US 8,801,664 B1
(45) Date of Patent: Aug. 12, 2014

(54) MEDICAL PROCEDURE KIT

(76) Inventor: Robert J. Perry, Oklahoma City, OK (US)

( * ) Notice: Subject to any disclaimer, the term of this patent is extended or adjusted under 35 U.S.C. 154(b) by 964 days.

(21) Appl. No.: 12/365,715

(22) Filed: Feb. 4, 2009

Related U.S. Application Data

(60) Provisional application No. 61/025,997, filed on Feb. 4, 2008.

(51) Int. Cl.
*A61M 5/00* (2006.01)
*A61M 5/32* (2006.01)

(52) U.S. Cl.
USPC .......................................... 604/116; 604/180

(58) Field of Classification Search
USPC ......... 604/116, 117, 510, 174, 178, 180, 177, 604/179, 173; 606/130
See application file for complete search history.

(56) References Cited

U.S. PATENT DOCUMENTS

| | | | |
|---|---|---|---|
| 3,955,558 A | | 5/1976 | Fuisz |
| 5,201,742 A | * | 4/1993 | Hasson ........................ 606/130 |
| 5,308,352 A | * | 5/1994 | Koutrouvelis ................ 606/130 |
| 5,848,966 A | | 12/1998 | Gusakov et al. |
| 6,761,715 B2 | | 7/2004 | Carroll |
| 7,004,961 B2 | | 2/2006 | Wong et al. |
| 7,458,968 B2 | | 12/2008 | Carroll |
| 2006/0122458 A1 | | 6/2006 | Bleich |
| 2008/0249467 A1 | | 10/2008 | Burnett et al. |
| 2008/0249501 A1 | | 10/2008 | Yamasaki |

* cited by examiner

*Primary Examiner* — Nicholas Lucchesi
*Assistant Examiner* — Brooke Matney
(74) *Attorney, Agent, or Firm* — San Diego IP Law Group, LLP

(57) ABSTRACT

A medical procedure kit is disclosed. Preferably, the medical procedure kit includes at least a frame configured to communicate with a body of a patient, an instrument positioning assembly supported by the frame, and means for advancing an instrument confined by the instrument positioning assembly into the body of the patient. Preferably, the medical procedure kit further includes an instrument carrier positioned between the instrument and the means for advancing the instrument. The instrument carrier preferably secures the instrument in a fixed position relative to the carrier, and the frame preferably includes a base portion configured to maintain the instrument positioning assembly in a stable position relative to the patient's body. The medical procedure kit preferably further includes a position adjustment member anchored by the frame and configured for interaction with the instrument positioning assembly to selectively position the instrument positioning assembly relative to the base portion of the frame.

9 Claims, 15 Drawing Sheets

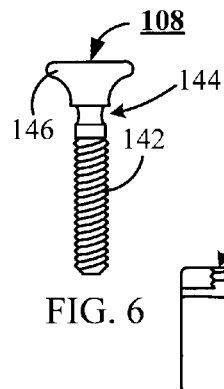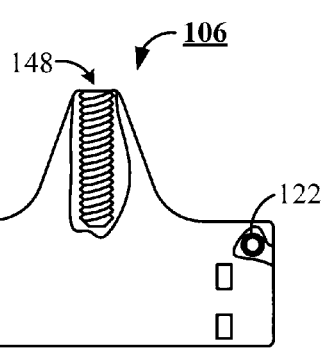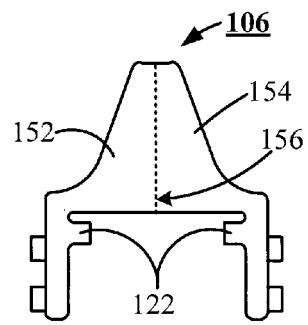
FIG. 6    FIG. 7    FIG. 8
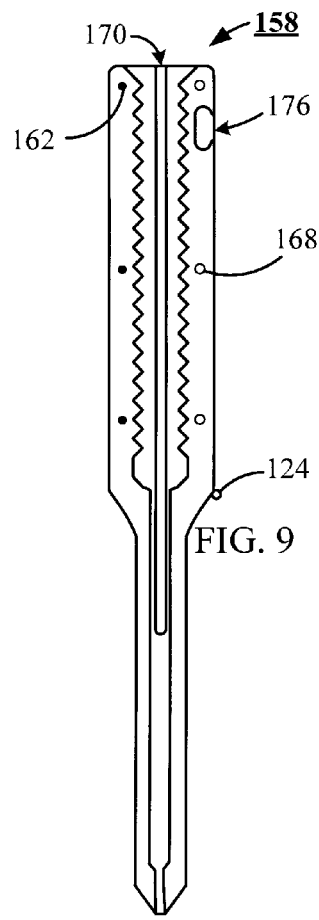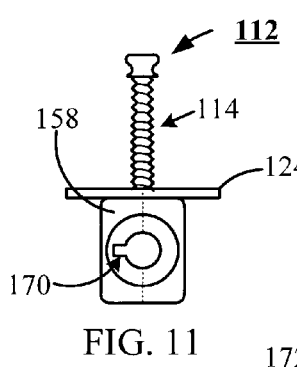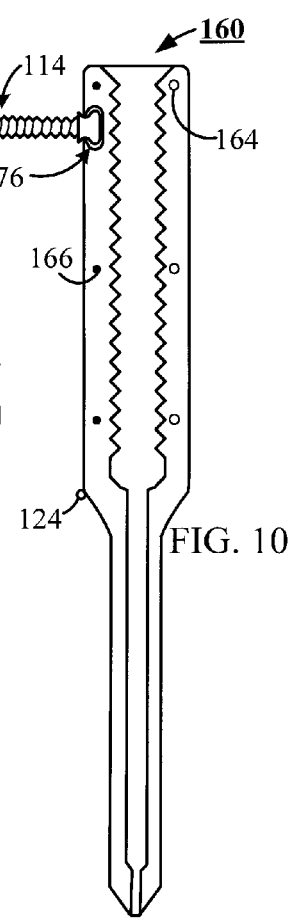
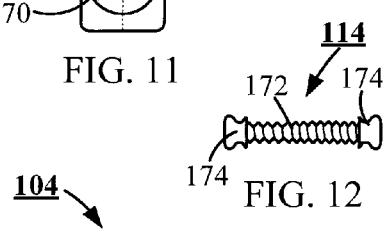
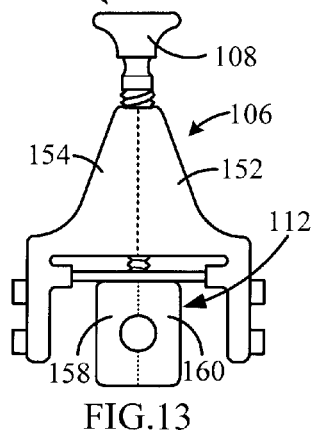
FIG. 9    FIG. 11    FIG. 12    FIG. 10
FIG. 13

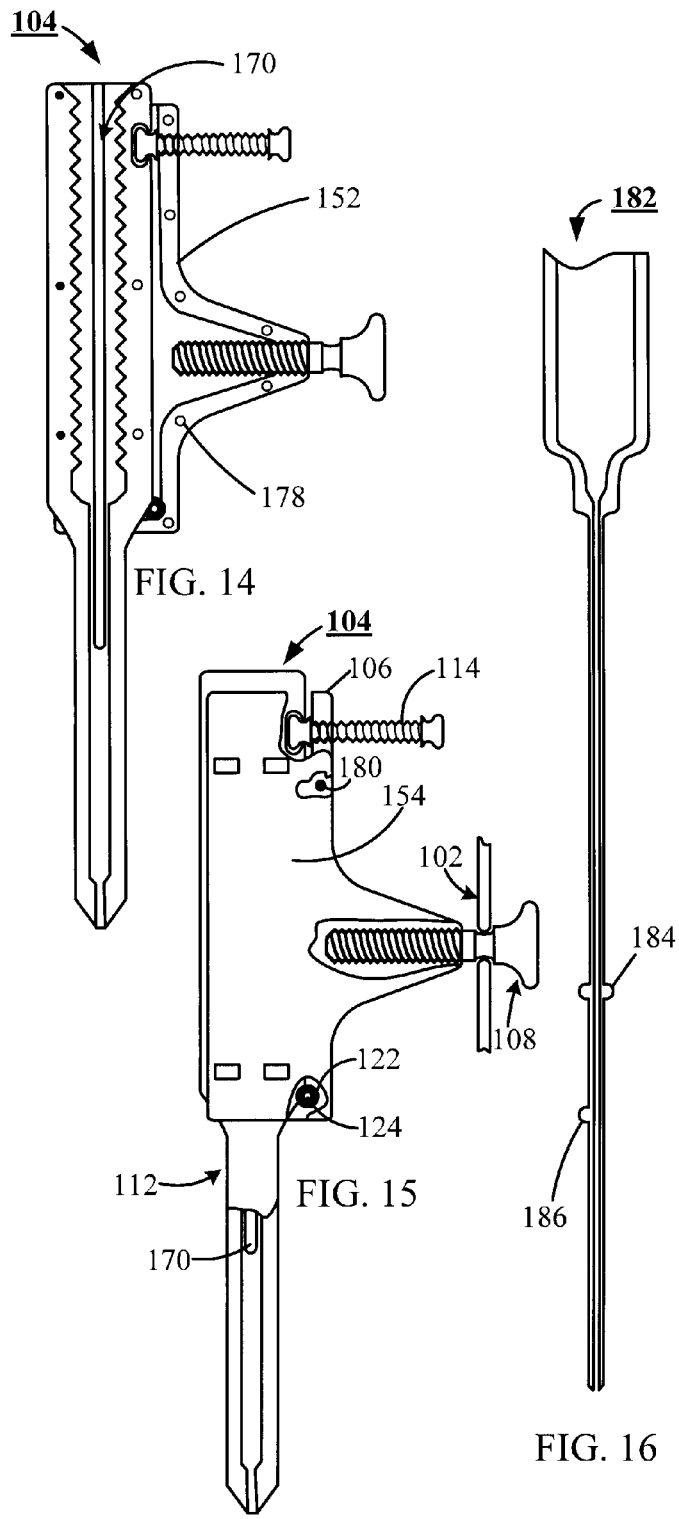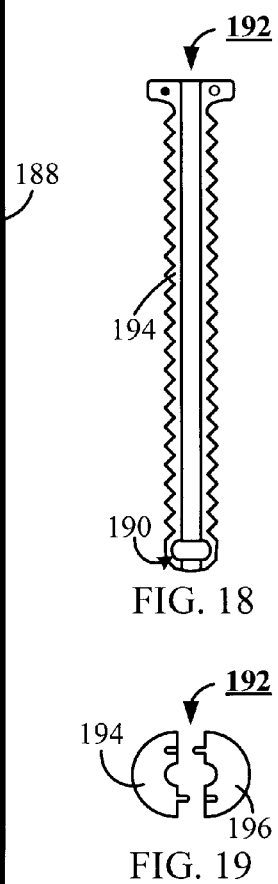

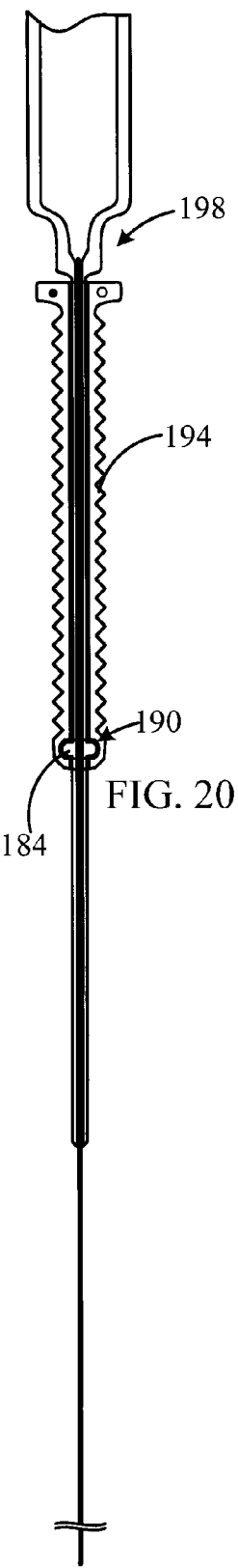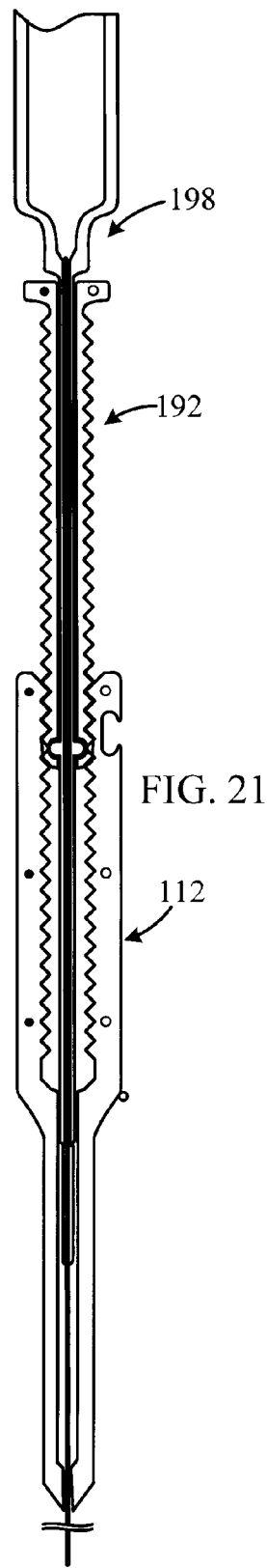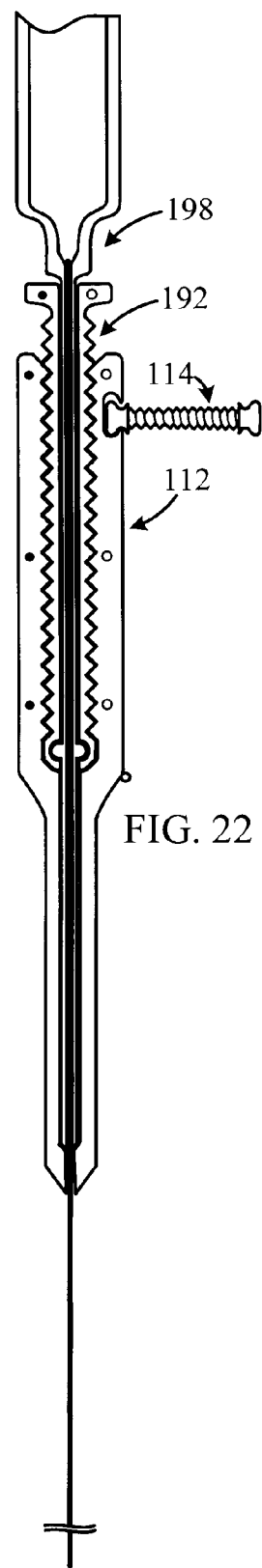

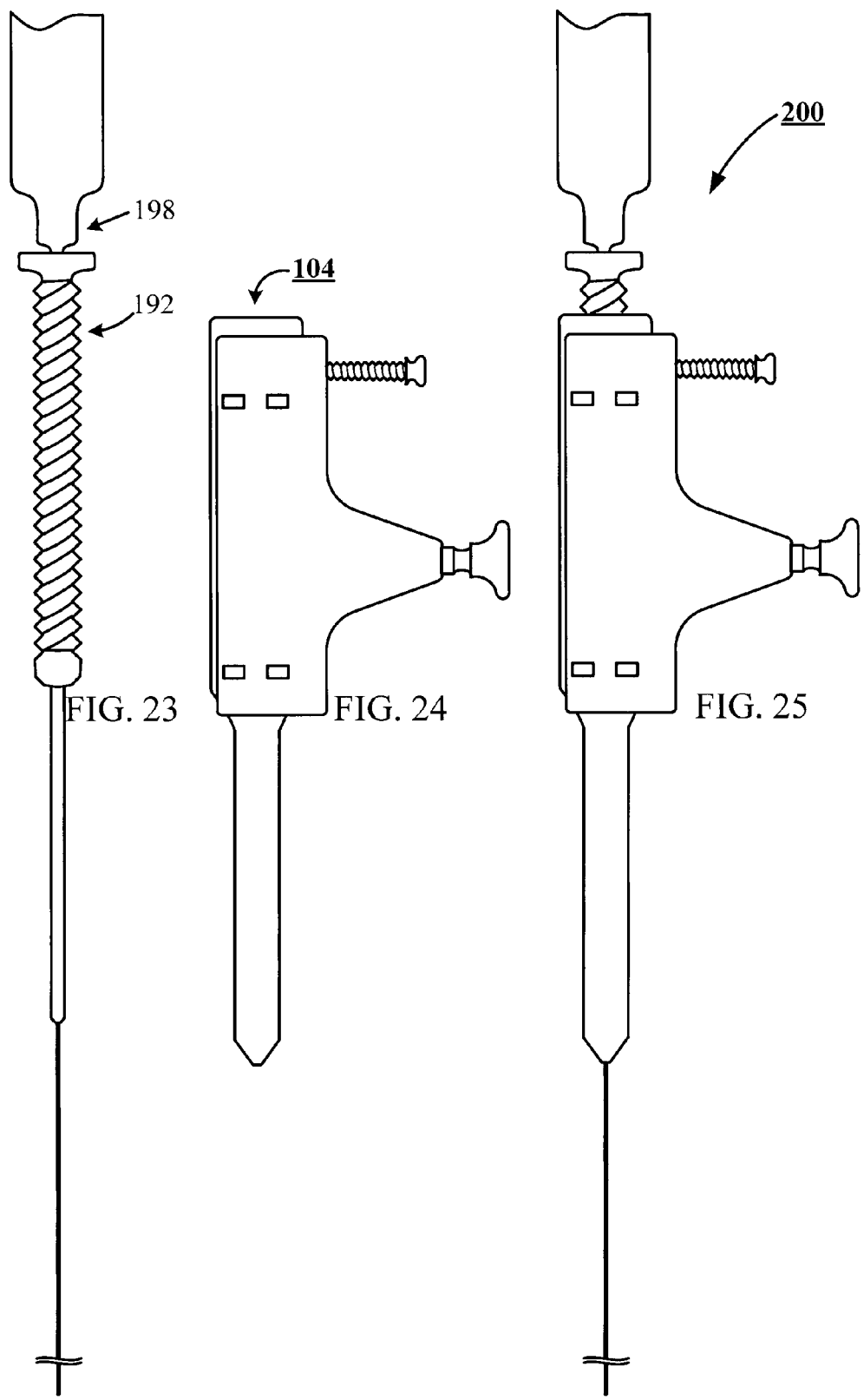

MEDICAL PROCEDURE KIT

RELATED APPLICATIONS

This application claims domestic priority to U.S. Provisional Application No. 61/025,997 filed Feb. 4, 2008, entitled "Medical Procedure Kit."

FIELD OF THE INVENTION

This invention relates to medical devices, and in particular, but not by way of limitation, to a medical procedure kit such as a spinal tap kit.

BACKGROUND

As the cost of healthcare continues to escalate, increased risks to health care providers from fluid born diseases mount, and a desire to reduce trauma experienced by patients undergoing medical procedures, the medical community is faced with an increasingly difficult environment in which to practice medicine.

An example of this increasingly difficult practice environment is spinal tap procedures. Currently, spinal tap procedures are time consuming, difficult and error prone. If the sub-dermal anesthetic is applied in a specific location along the spine, but the fluid extraction needle is inserted offset from the anesthetized region, the patient will generally experience pain and react with a sudden motion resulting in addition trauma to the region, and a potentially unsuccessful procedure, thereby causing at least a partial extraction and repositioning of the needle to continue with the procedure.

Additionally, the sudden physical response by the patient to the pain can cause penetration of the needle into an artery, resulting in bleeding and a possible contamination of the spinal fluid. In a number of spinal tap procedures, contamination of the spinal fluid with the patient's blood will require a repeat of the procedure. A repeat of the procedure is costly, both in time and instrumentality, and results in additional trauma being inflicted upon the patient.

Accordingly, challenges remain and a need persists for improvements in methods and apparatuses for use in accommodating effective and efficient deployment and use of health care provider's time, medical procedure kits, and a reduction in the exposure of health care providers to medical hazards.

SUMMARY OF THE INVENTION

In accordance with preferred embodiments, a medical procedure kit is provided. Preferably, the medical procedure kit includes at least a frame configured to communicate with a body of a patient, an instrument positioning assembly supported by the frame, means for advancing an instrument confined by the instrument positioning assembly into the body of the patient, and an instrument carrier positioned between the instrument and the means for advancing the instrument.

The instrument carrier preferably secures the instrument in a fixed position relative to the carrier, and the frame preferably includes a base portion configured to maintain the instrument positioning assembly in a stable position relative to the patient's body. The medical procedure kit preferably further includes a position adjustment member anchored by the frame and configured for interaction with the instrument positioning assembly to selectively position the instrument positioning assembly relative to the base portion of the frame, to align the instrument to a predetermined location on the patient's body.

In a preferred embodiment, the instrument positioning assembly includes at least a position shuttle supported by the frame and communicating with the position adjustment member, an instrument guide supported by said position shuttle, and a pitch adjustment member anchored by the position shuttle and configured for interaction with said instrument guide to selectively position a pitch of the instrument carrier relative to said base portion and in alignment with the predetermined location on the patient's body.

These and various other features and advantages that characterize the claimed invention will be apparent upon reading the following detailed description and upon review of the associated drawings.

BRIEF DESCRIPTION OF THE DRAWINGS

FIG. 6 shows a view in elevation of a position adjustment member for use in adjusting a position of an instrument of the inventive medical procedure kit of FIG. 1, relative to a patient's body.

FIG. 7 illustrates a partial cutaway view in elevation of a right side of a position shuttle of the inventive medical procedure kit of FIG. 1.

FIG. 8 depicts a bottom plan view of the position shuttle of the inventive medical procedure kit of FIG. 1.

FIG. 9 portrays a view in elevation of a first member of an instrument guide configured for confinement by the position shuttle of the inventive medical procedure kit of FIG. 1.

FIG. 10 illustrates a view in elevation of a second member of the instrument guide configured for interaction with the first member of FIG. 9 to form the instrument guide of FIG. 11.

FIG. 11 shows a top plan view of the instrument guide securing the pitch adjustment member of FIG. 10.

FIG. 12 reveals a side view of a pitch adjustment member configured to interact with the position shuttle of FIG. 7.

FIG. 13 depicts a bottom plan view of an instrument positioning assembly of the inventive medical procedure kit of FIG. 1.

FIG. 14 portrays a view in elevation of a first half of the instrument positioning assembly of FIG. 13 of the inventive medical procedure kit of FIG. 1.

FIG. 15 reveals a partial cutaway view in elevation of the instrument positioning assembly of FIG. 14 of the inventive medical procedure kit of FIG. 1.

FIG. 16 shows a cutaway view in elevation of an instrument carrier of the inventive medical procedure kit of FIG. 1.

FIG. 17 illustrates a view in elevation of a medical procedures instrument configured for adaptation to the instrument carrier of FIG. 16.

FIG. 18 depicts a view in elevation of a first half of an advancement means for use in advancing the medical procedures instrument of FIG. 17 into the body of a patient.

FIG. 19 portrays a top plan view of a first and second half of the advancement means of FIG. 18.

FIG. 20 reveals a partial cutaway view in elevation of a medical procedure implement formed from the medical procedures instrument of FIG. 17 secured by the instrument carrier of FIG. 16 and positioned within the advancement means of FIG. 18.

FIG. 21 shows a partial cutaway view in elevation of the medical procedures instrument of FIG. 17 secured by the instrument carrier of FIG. 16, positioned within the advancement means of FIG. 18, and inserted in the first half of the instrument guide of FIG. 9.

FIG. 22 illustrates a partial cutaway view in elevation of the medical procedures instrument, instrument carrier, advancement means, and the first half of the instrument guide configuration of FIG. 21 showing the maximum protrusion of the medical procedures instrument beyond the end of the instrument guide of FIG. 9.

FIG. 23 depicts a view in elevation of a medical instrument deployment assembly formed by the medical procedures instrument secured by the instrument carrier.

FIG. 24 portrays a view in elevation of the instrument positioning assembly.

FIG. 25 reveals a view in elevation of a medical instrument deployment assembly in combination with the instrument positioning assembly.

DETAILED DESCRIPTION OF A PREFERRED EMBODIMENT

Detailed descriptions of the preferred embodiments are provided herein. It is to be understood, however, that the present invention may be embodied in various forms. Various aspects of the invention may be inverted, or changed in reference to specific part shape and detail, part location, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
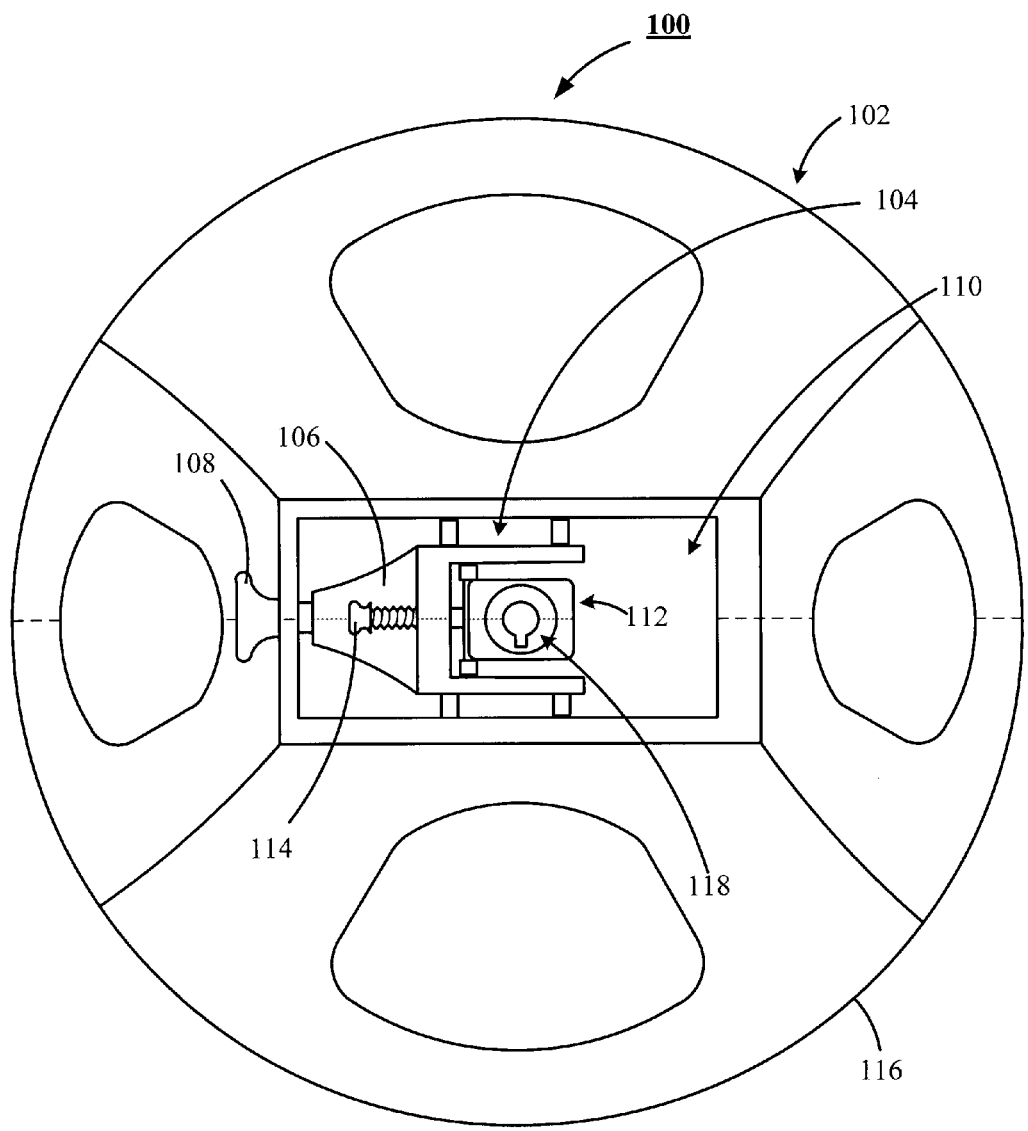
FIG. 1 shows a top plan view of an inventive medical procedure kit of the present invention.

Reference will now be made in detail to one or more examples of the invention depicted in the figures. Each example is provided by way of explanation of the invention, and not meant as a limitation of the invention. FIG. 1 shows a preferred embodiment of an inventive medical procedure kit 100 that preferably includes a frame 102 configured for adaptation with a back of a patient. The preferred frame 102 supports an instrument positioning assembly 104 that includes a position shuttle 106 supported by the frame 102 and communicating with a position adjustment member 108. Rotation of the position adjustment member 108 controls the position of the position shuttle 106 relative to an instrument alignment aperture 110 of the frame 102. The instrument positioning assembly 104 further includes an instrument guide 112 supported by the position shuttle 106, and a pitch adjustment member 114 anchored by the position shuttle 106 and configured for interaction with the instrument guide 112 to selectively position a pitch of the instrument guide 112 relative to a base portion 116 of said frame 102. FIG. 1, further shows that the instrument guide 112 provides an instrument assembly attachment aperture 118.

Figure 2:
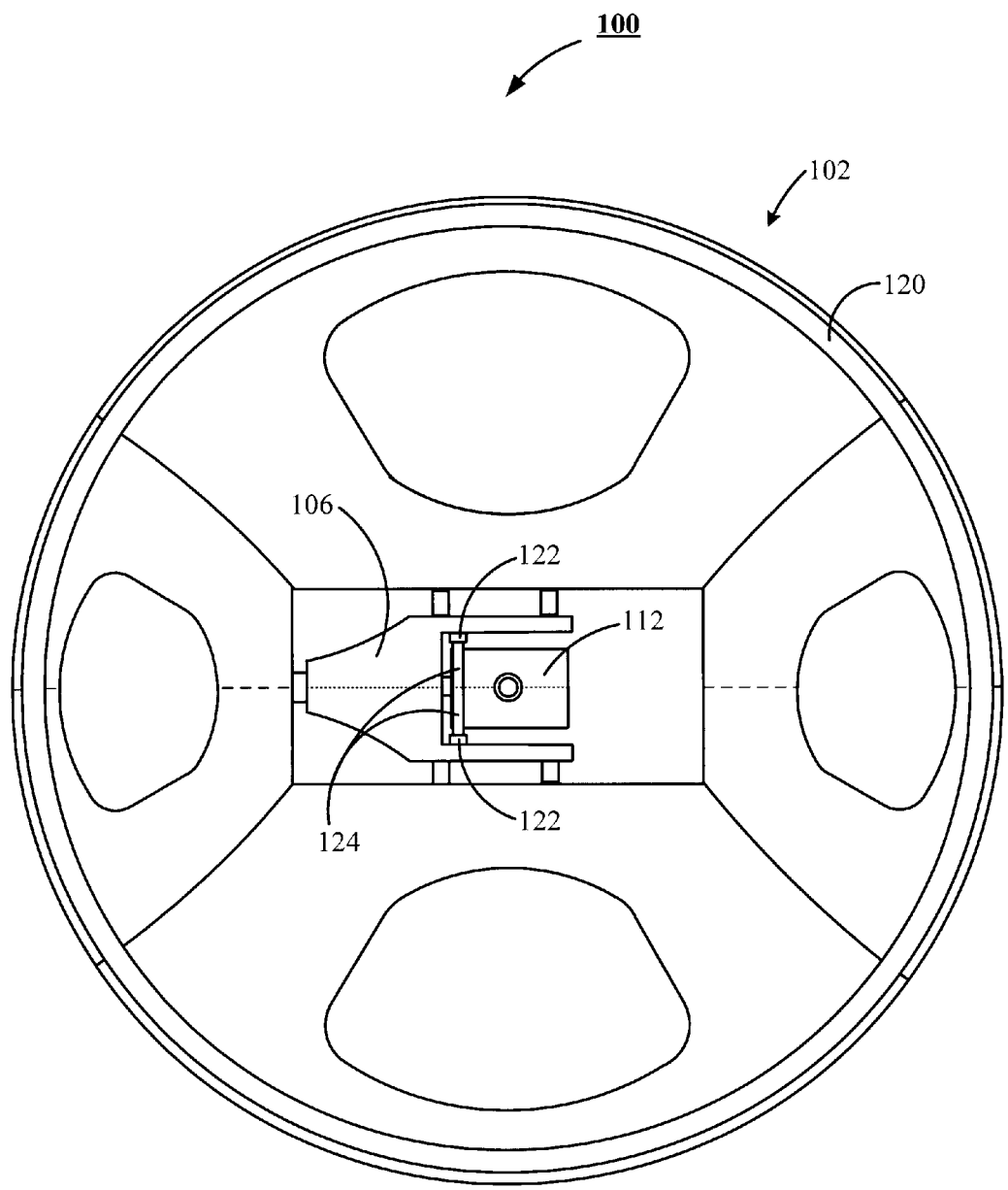
FIG. 2 illustrates a bottom plan view of the inventive medical procedure kit of FIG. 1.
Figure 3:
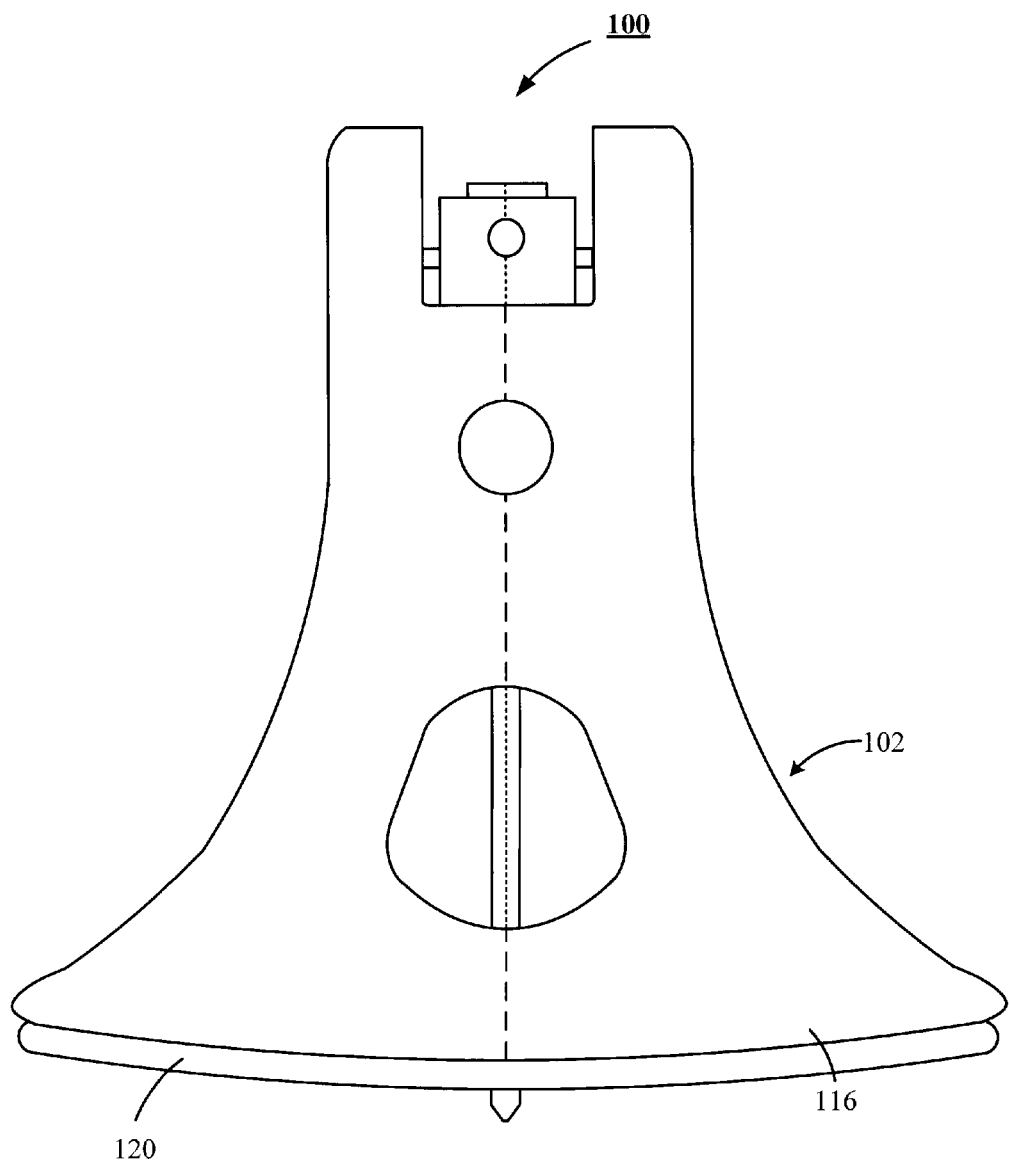
FIG. 3 depicts a front view in elevation of the inventive medical procedure kit of FIG. 1.

FIG. 2 shows the frame 102 supports a patient attachment member 120, which in a preferred embodiment is formed from a double back foam material. The position shuttle 106 provides a pair of pivot support members 122 members that interact with a pair of pivot members 124 of the instrument guide 112. FIG. 3 provides better perspective of the patient attachment member 120 relative to the frame 102.

Figure 4:
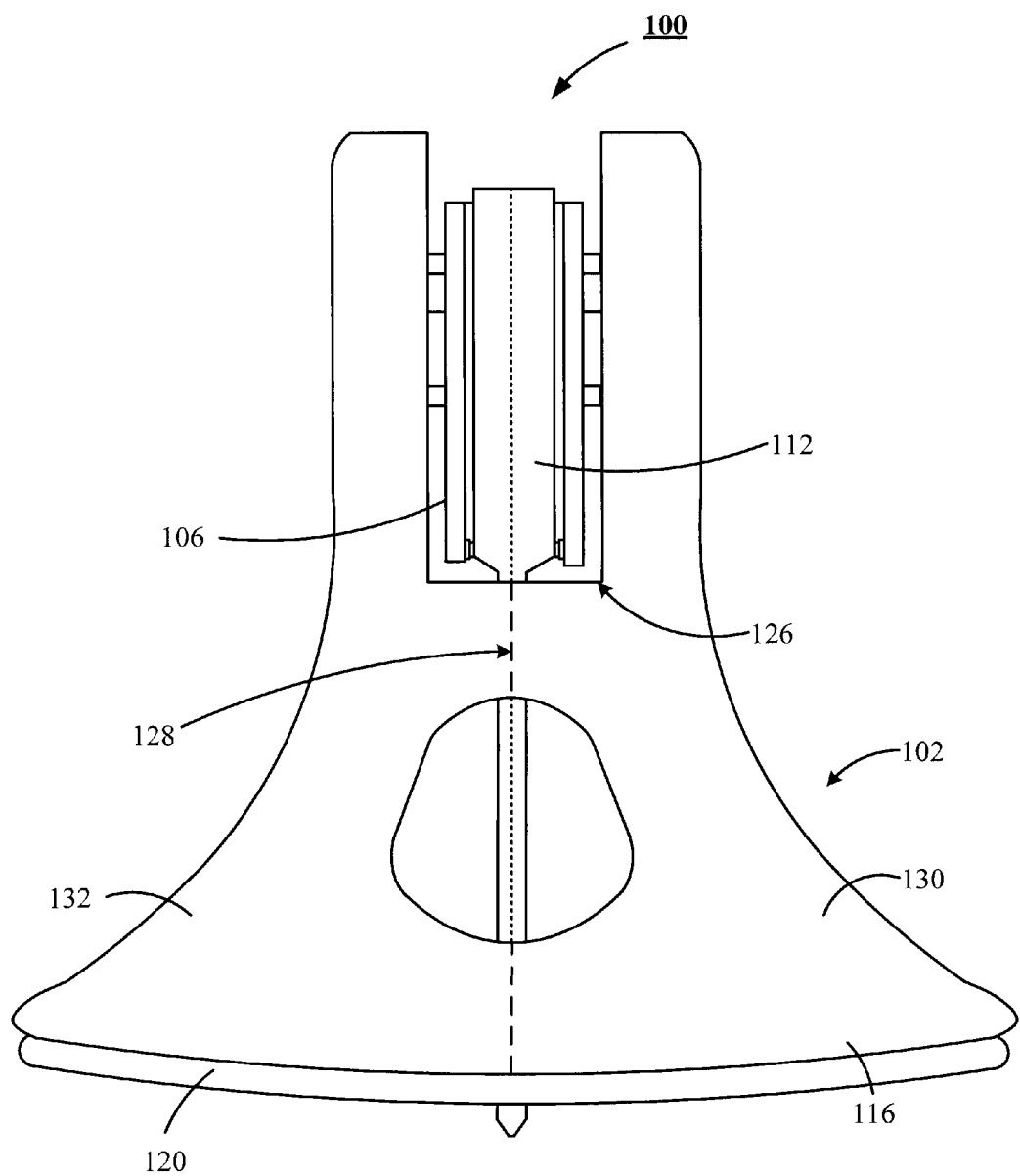
FIG. 4 portrays a back view in elevation of the inventive medical procedure kit of FIG. 1.

The back view in elevation of the inventive medical procedure kit 100, shown by FIG. 4, reveals an instrument guide pitch aperture 126 provided by the frame 102, which allows the instrument guide 112 to rotate relative to the position shuttle 106 without being encumbered by the frame 102. It is also noted that FIG. 4 shows the frame 102 includes a joint line 128, shown in a dashed line presentation. Preferably, the frame 102 is formed from two side members 130 and 132, which promotes ease of assembly of the inventive medical procedure kit 100.

Figure 5:
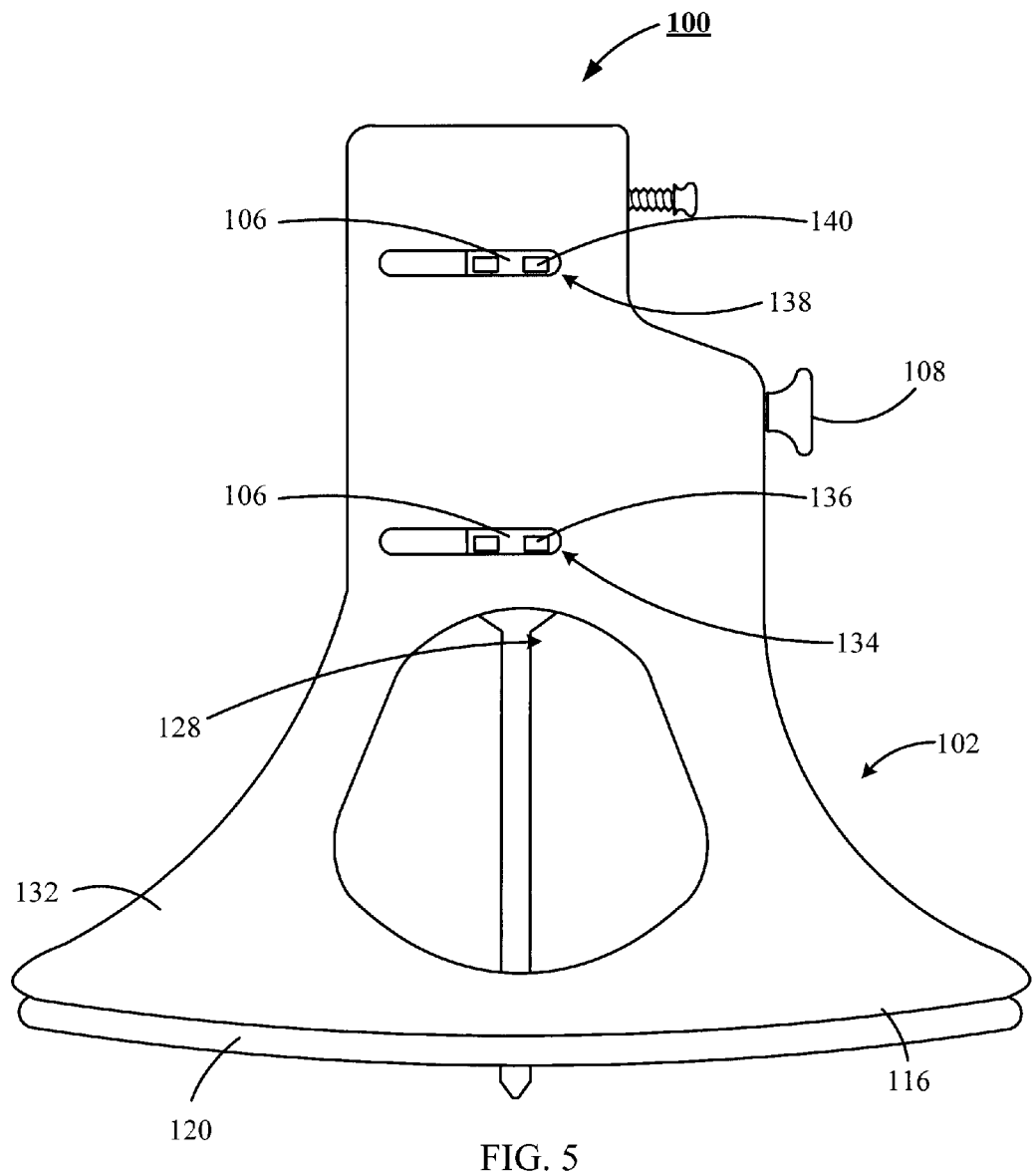
FIG. 5 reveals a right side view in elevation of the inventive medical procedure kit of FIG. 1.

FIG. 5 reveals that the side member 132 preferably provides a first shuttle slide aperture 134 that accommodates at least one slide 136 of the position shuttle 106, and a second shuttle slide aperture 138 that accommodates at least a second slide 140 of the position shuttle 106. In operative use, rotation of the position adjustment member 108 is used to selectively locate the position shuttle 106 along the shuttle slide apertures 134 and 138.

As shown by FIG. 6, in a preferred embodiment the position adjustment member 108 provides a threaded body 142 configured for interaction with the position shuttle 106 of FIG. 7. FIG. 6 further shows that the position adjustment member 108 preferably includes a retention channel 144 configured to interact with the frame 102 (of FIG. 5) such that the frame 102 anchors a head portion 146 of the position adjustment member 108, during rotation of the position adjustment member 108.

FIG. 7 shows the position shuttle 106 preferably provides a positioning aperture 148 configured for interaction with the threaded body 142 of the position adjustment member 108 (of FIG. 6), and a pitch adjustment aperture 150 that interacts with the pitch adjustment member 114 (of FIG. 10), to accommodate an angled alignment of the instrument guide 112 (of FIG. 11) relative to a patient's back. FIG. 7 also provides a cutaway view of one of the pivot support members 122, while FIG. 8 provides a bottom plan view of both of the pivot support members 122. FIG. 8 also shows that the position shuttle 106 is formed from side members 152 and 154, which were joined together forms a joint line 156.

FIG. 9 shows a first instrument guide body 158, while FIG. 10 shows a second instrument guide body 160. The first instrument guide body 158 provides a plurality of male attachment members 162 that interact with a plurality of female attachment apertures 164 of the second instrument guide body 160. The second instrument guide body 160 provides a plurality of male attachment members 166 that interact with a plurality of female attachment apertures 168 of the first instrument guide body 158 to form the instrument guide 112 of FIG. 11. The first instrument guide body 158 further provides an instrument orientation channel 170, which functions to maintain a predetermined orientation of a medical procedures instrument, such as a hypodermic needle 188 as shown by FIG. 17.

In a preferred embodiment, the pitch adjustment member 114 includes a main threaded body portion 172 fitted with a common end cap 174 on each end of the main threaded body portion 172, as shown by FIG. 12. An advantage of having the pitch adjustment member 114 configured with the common end cap 174 on each end of the main threaded body portion 172 is that upon assembly of the instrument guide 112 (of FIG. 11), the pitch adjustment member 114 cannot be misassembled into a pitch adjustment confinement cavity 176 of both the first and second instrument guide bodies 158 and 160 of FIGS. 9 and 10 respectfully.

In forming the instrument positioning assembly 104 of FIG. 13, preferably the second instrument guide body 160 is positioned for acceptance of one of the common caps 174 (also referred to herein as head portion 174) of the pitch adjustment member 114 (of FIG. 12), which is positioned into the pitch adjustment confinement cavity 176 (of FIGS. 9 and 10). With the pitch adjustment member 114 positioned within the second instrument guide body 160, the first instrument guide body 158 is aligned on top of the second instrument guide body 160 and preferably snapped together to form the instrument guide 112. Next, the side member 152 of the position shuttle 106 is positioned for acceptance of the instrument guide 112. With the instrument guide 112 positioned within the first side member 152, the second side member 154 is positioned atop the instrument guide 112, aligned with the first side member 152, and preferably snapped together. To complete the preferred instrument positioning assembly 104, the position adjustment member 108 is threaded into the position shuttle 106.

FIG. 14 shows that the first side member 152 provides a plurality of female attachment apertures 178, which each interact with a corresponding one of a plurality of male attachment members 180 of the second side member 154 as shown in cutout view by FIG. 15. FIG. 15 shows the preferred instrument positioning assembly 104 includes the pitch adjustment member 114 anchored to the position shuttle 106 such that when the pitch adjustment member 114 is rotated the instrument guide 112 rotates about the pair of pivot support members 122 via the pair of pivot members 124 of the instrument guide 112. FIG. 15 further shows the position adjustment member 108 anchored to the frame 102 such that when the position adjustment member 108 is rotated, the position shuttle 106 changes position relative to the frame 102.

Turning to FIG. 16, shown therein is an instrument carrier 182 preferably formed from the clear, rigid polymer and the hypodermic needle 188 (of FIG. 17), is insert molded within the instrument carrier 182 to form a medical procedure implement 198 (of FIG. 20). In a preferred embodiment, the instrument carrier 182 provides a positioning feature 184, and an instrument orientation feature 186. In a preferred embodiment, the instrument positioning feature 184 interacts with a feature capture cavity 190 of an instrument advancement member 192 of FIG. 18, and the instrument orientation feature 186 interacts with the instrument orientation channel 170 of FIG. 14. The feature capture cavity 190 is fully formed when two correspondingly formed threaded members 194 and 196 are aligned one to the other and snapped together, as shown by FIG. 19, to form the instrument advancement member 192.

FIGS. 20, 21, and 22 should preferably be viewed collectively. FIG. 20 shows the medical procedure implement 198 positioned within the threaded member 194, with the positioning feature 184 of the medical procedure implement 198 cradled by the feature capture cavity 190. FIG. 21 shows the combined medical procedure implement 198 and instrument advancement member 192 interacting with the instrument guide 112. As shown by FIG. 22, through rotation of the instrument advancement member 192, the medical procedure implement 198 is advanced to its full extent relative to the instrument guide 112.

It is further recommended that FIGS. 23, 24, and 25 be viewed collectively, to provide a more comprehensive understanding of the preferred embodiment of the present invention. FIG. 23 shows the medical procedure implement 198 combined with the instrument advancement member 192, which when joined to the instrument positioning assembly 104 of FIG. 24 forms a medical instrument delivery module 200 depicted by FIG. 25.

Figure 26:
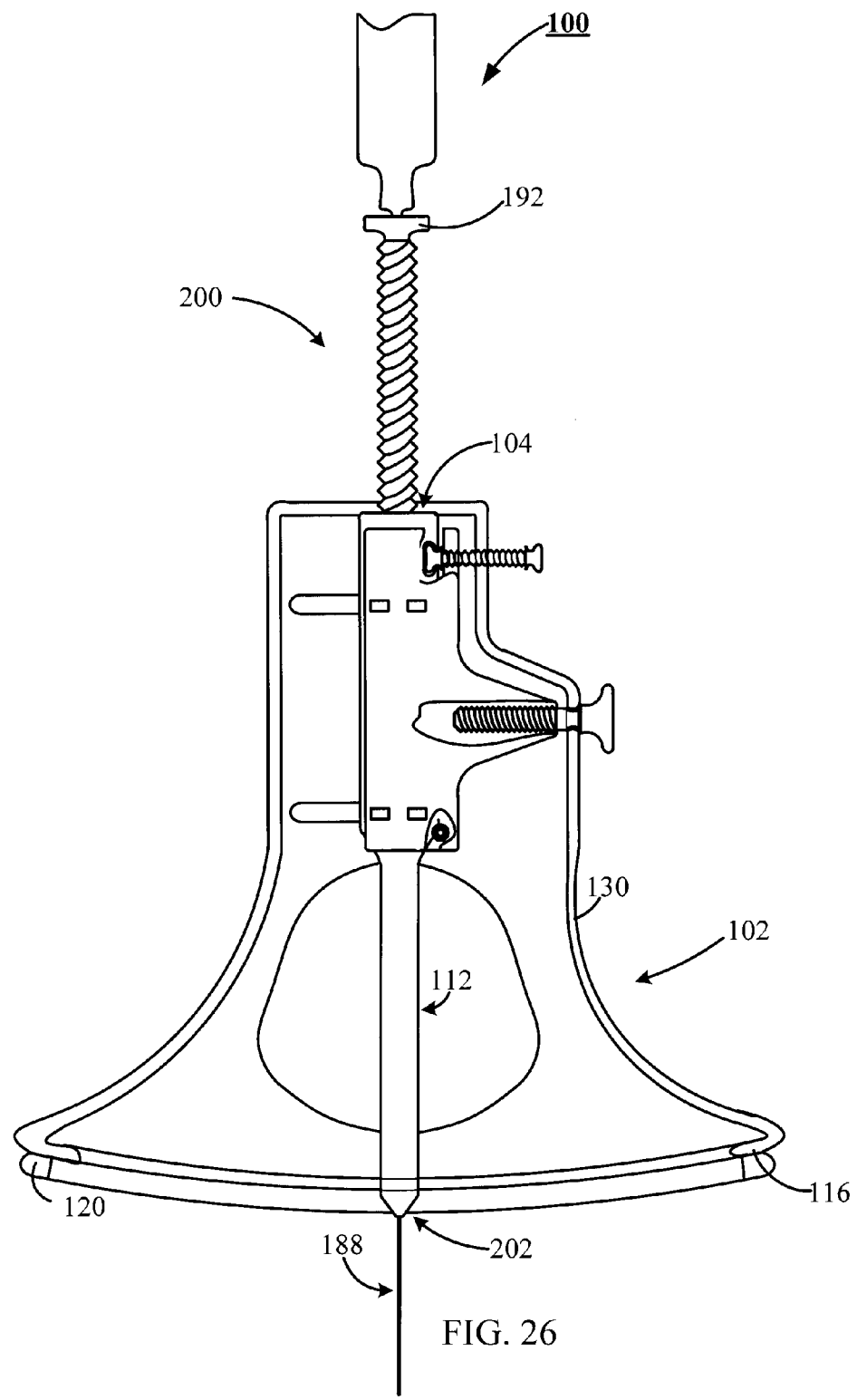
FIG. 26 shows a partial cutaway view in elevation of the inventive medical procedure kit showing the medical procedures instrument projecting beyond the frame when the instrument carrier interacts with the instrument guide.
Figure 27:
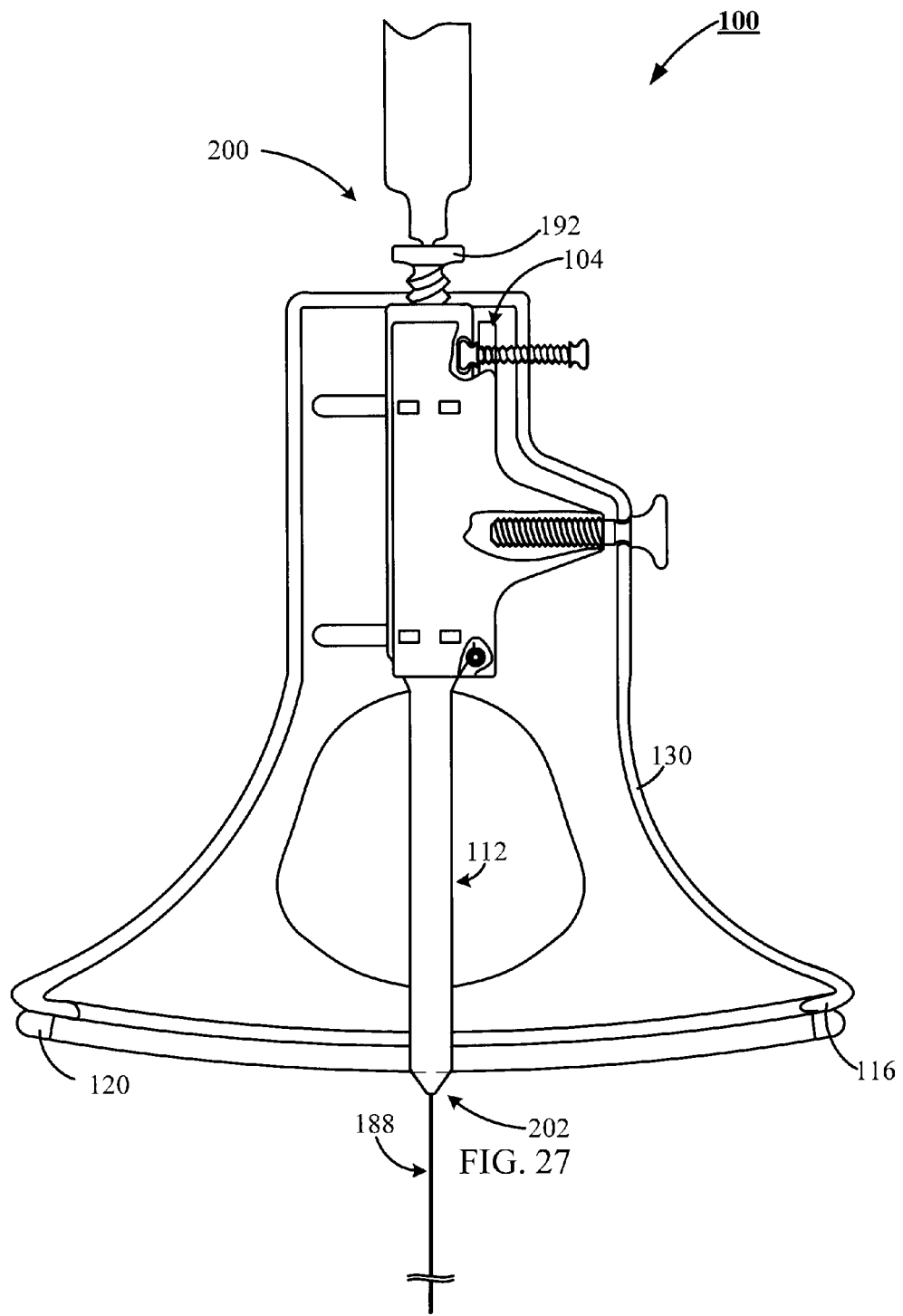
FIG. 27 illustrates a partial cutaway view in elevation of the inventive medical procedure kit showing the medical procedures instrument extended beyond the frame when the instrument carrier interacts with the instrument guide.

The preferred embodiment shown by FIG. 26 reveals the medical instrument delivery module 200 positioned within the side member 130 of the frame 102. Preferably, a tip 202 of the instrument guide 112 of the instrument positioning assembly 104 protrudes beyond the patient attachment member 120 to promote alignment of the inventive medical procedure kit 100 with a predetermined point on the back of the patient. FIG. 26 further shows the hypodermic needle 188 extends beyond the tip 202 and would, during a spinal tap procedure, allow the needle to penetrate into the soft tissue of a patient's back. Preferably, just prior to encountering non-soft tissue within the patient's back, the instrument advancement member 192 engages the instrument guide 112 and advancement of the hypodermic needle 188 proceeds by rotation of the instrument advancement member 192 until the hypodermic needle 188 extends its maximum amount beyond the tip 202, as shown by FIG. 27.

Figure 28:
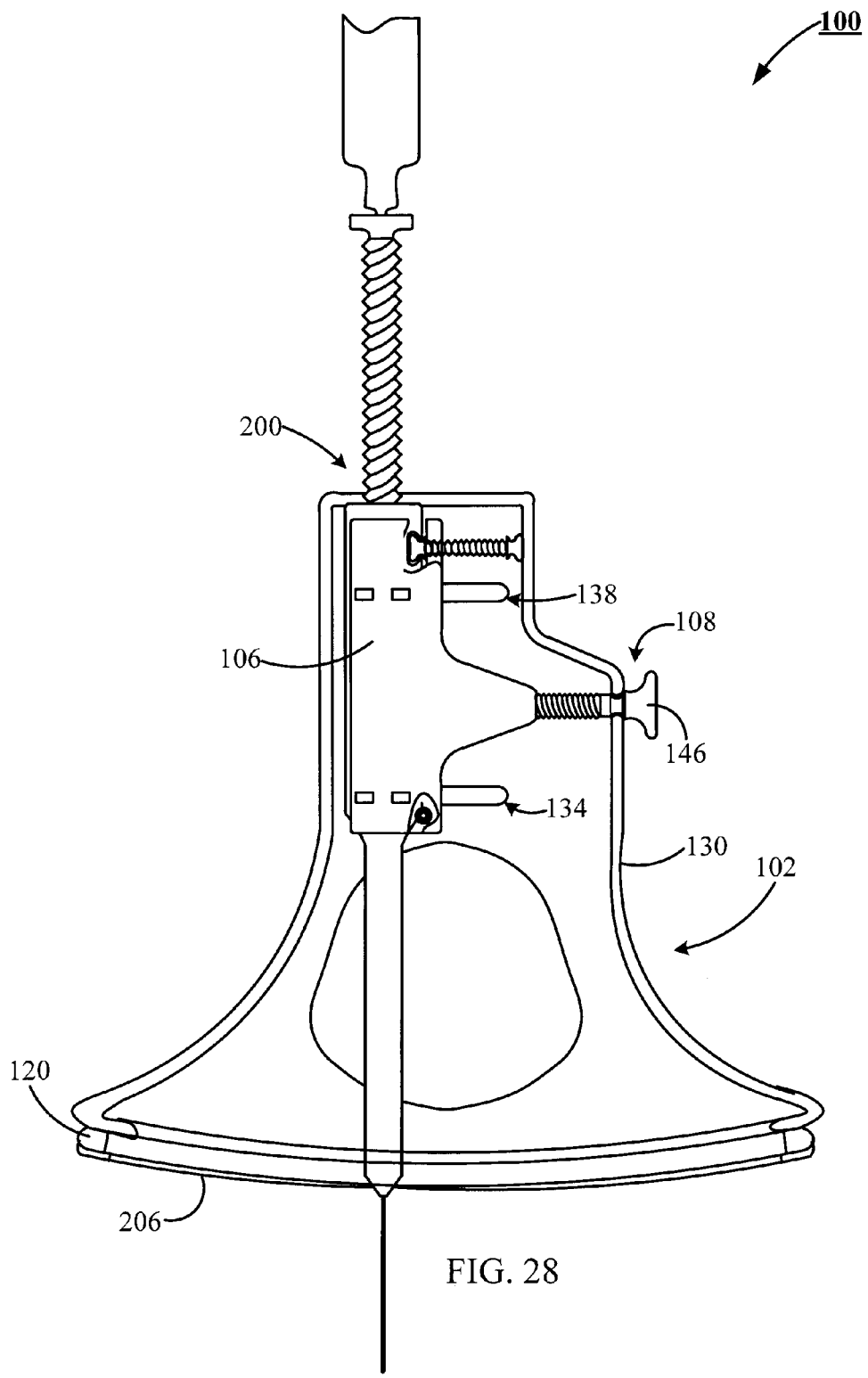
FIG. 28 depicts a partial cutaway view in elevation of the inventive medical procedure kit revealing the medical procedures instrument extended beyond the frame and offset from a central location of the frame.

FIG. 28 shows the medical instrument delivery module 200 positioned within the side member 130 of the frame 102 at its maximum extent from a head portion 146 of the position adjustment member 108. The rotation of the position adjustment member 108 is used to selectively locate the position shuttle 106 along the shuttle slide apertures 134 and 138. FIG. 28 further shows that in a preferred embodiment, a release liner 206 is positioned upon the patient attachment member 120 to protect the adhesive from contamination. Just prior to attaching the medical procedure kit 100 to the back of the patient, the release liner 206 is removed to expose the adhesive surface of the patient attachment member 120.

Figure 29:
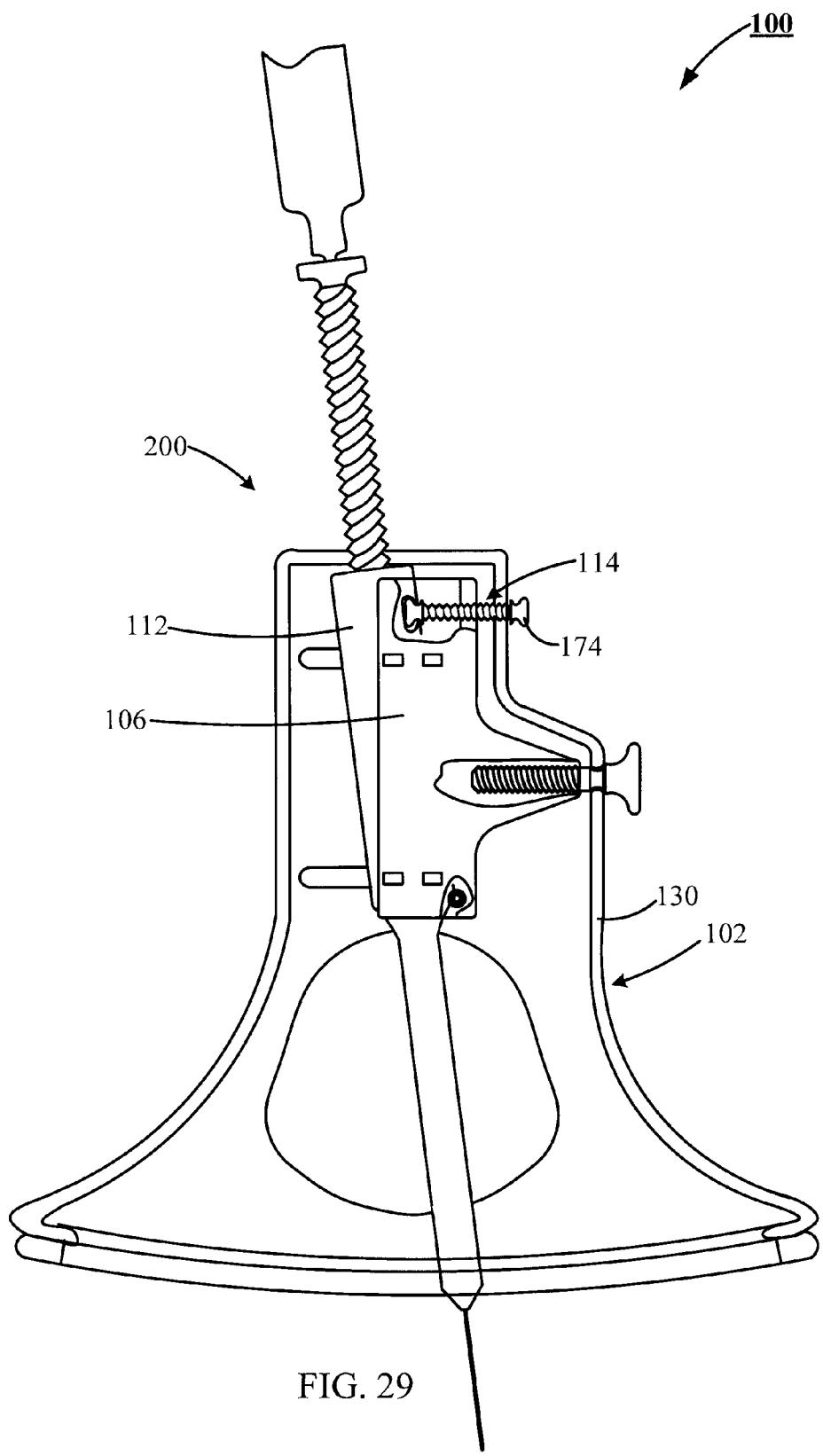
FIG. 29 portrays a partial cutaway view in elevation of the inventive medical procedure kit revealing the medical procedures instrument extended beyond the frame and angled from a normal alignment with the central location of the frame.

FIG. 29 shows the medical instrument delivery module 200 positioned within the side member 130 of the frame 102 at its maximum pitch from the head portion 174 of the pitch adjustment member 114. Rotation of the pitch adjustment member 114 is used to selectively position the pitch of the instrument guide 112 relative to the position shuttle 106, thus allowing an adaptation of the inventive medical procedure kit 100 to the particular patient undergoing the procedure.

Figure 30:
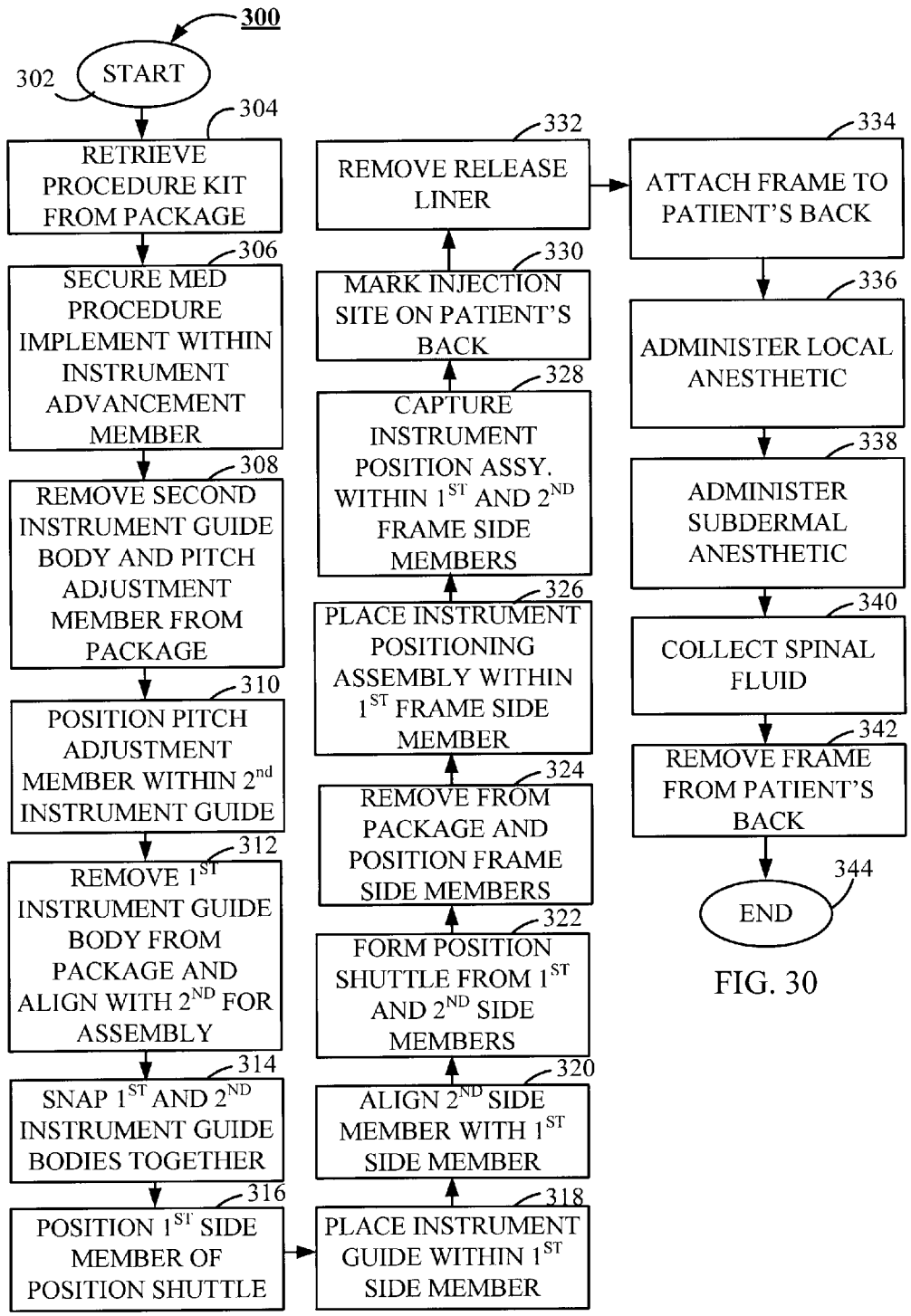
FIG. 30 shows a flowchart of a method of making the inventive medical procedure kit of FIG. 29.

FIG. 30 illustrates a flow chart 300, showing process steps of a method for utilizing an inventive medical procedure kit (such as 100). The method commences at start process step 302 and proceeds to process step 304 with retrieving the inventive medical procedure kit from a sterilized package. At process step 306, a medical procedure implement (such as 198) is secured within an instrument advancement member (such as 192) and set aside for future use.

Following the union of the medical procedure implement with the instrument advancement member, the process proceeds to process step 308, with the removal of a second instrument guide body (such as 160) and a pitch adjustment member (such as 114) from the sterilized package. At process step 310, the pitch adjustment member is positioned within the second instrument guide body. At process step 312, a first instrument guide body (such as 158) is removed from the sterilized package and aligned for assembly with the second instrument guide lobby and the pitch adjustment member. At process step 314, an instrument guide (such as 112) is formed by snapping together the first guide body with the second guide body to capture the pitch adjustment member.

At process step 316, a first side member (such as 152) of a position shuttle (such as 106) is removed from the sterilized package and positioned for acceptance of the instrument guide. At process step 318, the instrument guide is positioned within the first side member. At process step 320, a second side member (such as 154) is removed from the sterilized package, and aligned for assembly with the first side member. At process step 322, an instrument positioning assembly (such as 104) is formed by snapping together the first side member to the second side member with the instrument guide captured between the two, and preferably threading a position adjustment member (such as 108) into a corresponding positioning aperture (such as 148) that was formed when the first and second side members were snapped together.

Continuing with process step 324, side members (such as 130 and 132) of a frame (such as 102) are removed from sterilized package and positioned for acceptance of the instrument positioning assembly. At process step 326, the instrument positioning assembly is positioned within the side member 130, and at process step 328, the side member 132 is aligned and joined with the side member 130 to capture the instrument positioning assembly. At process step 330, a position along the backbone of the patient is selected and marked. At process step 332, a release liner (such as 206) is removed from the patient attachment member (such as 120), to expose an adhesive surface.

At process step 334, a tip (such as 202) of the instrument guide is aligned with the marked position along the patient's backbone, and the patient attachment member is pressed into contact of the back of the patient thereby securing the frame to the back of the patient. At process step 336, optionally a first medical procedure implement secured within an instrument advancement member, is advanced through the instrument guide and into contact with the patient's back for application of a local anesthetic. However, the local anesthetic may be administered without the use of the inventive medical procedure kit. At process step 338, the first of the medical procedure implement secured within an instrument advancement member is removed from the instrument guide, and a second medical procedure implement secured within an instrument advancement member is advanced through the instrument guide and into the patient's back for application of a subdermal anesthetic.

At process step 340, the second medical procedure implement secured within an instrument advancement member is removed, and a third medical procedure implement secured within an instrument advancement member is advanced through the instrument guide, and into the patient's spinal column for the collection of spinal fluid. It is noted that use of the inventive medical procedure kit promotes entry of the subdermal anesthetic needle through the same entry point as the entry point of the local anesthetic needle, and entry of the spinal tap needle through the same entry point used by the subdermal anesthetic needle.

Upon collection of the spinal tap fluid, the third medical procedure implement secured within an instrument advancement member is removed from the instrument guide, and the frame supporting the instrument positioning assembly is removed from the patient's back at process step 342, and the process concludes at end process step 344.

Figure 31:
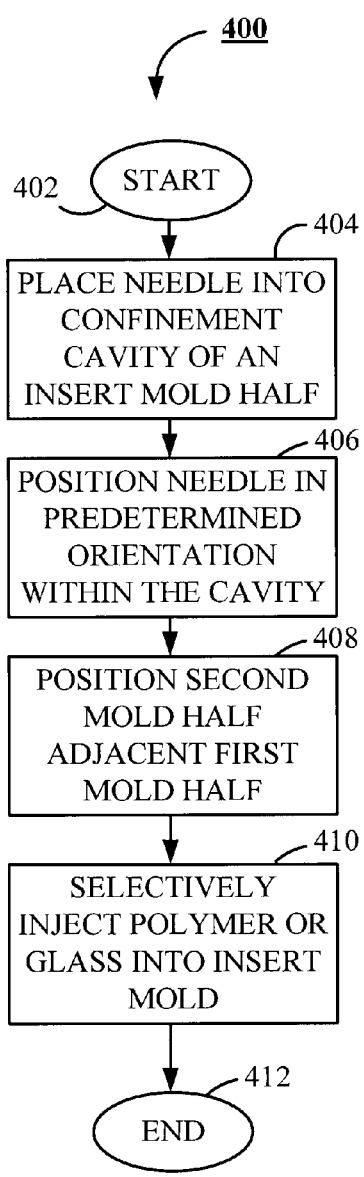
FIG. 31 illustrates a plan view of an insert mold for use in insert molding a medical procedure implement of the inventive medical procedure kit of FIG. 29.

FIG. 31 illustrates a flow chart 400, showing process steps of a method of forming a medical procedure implement (such as 198). The method commences at start process step 402 and proceeds to process step 404 with the placement of a needle (such as 188) into a needle confinement cavity (such as 212) of a first half (such as 210) of an insert mold (such as 208). At process step 406, the needle is positioned in predetermined orientation. At process step 408, a second half (such as 214) of the insert mold 208 is joined to the first half of the mold to capture the needle in its predetermined position. At process step 410, a polymer is preferably injected into the insert mold 208 to form the medical procedure implement, and the process concludes at end process step 412. In an alternate embodiment at process step 410, a molten glass is injected into the insert mold to form the medical procedure implement, and the process concludes at end process step 412.

Figure 32:
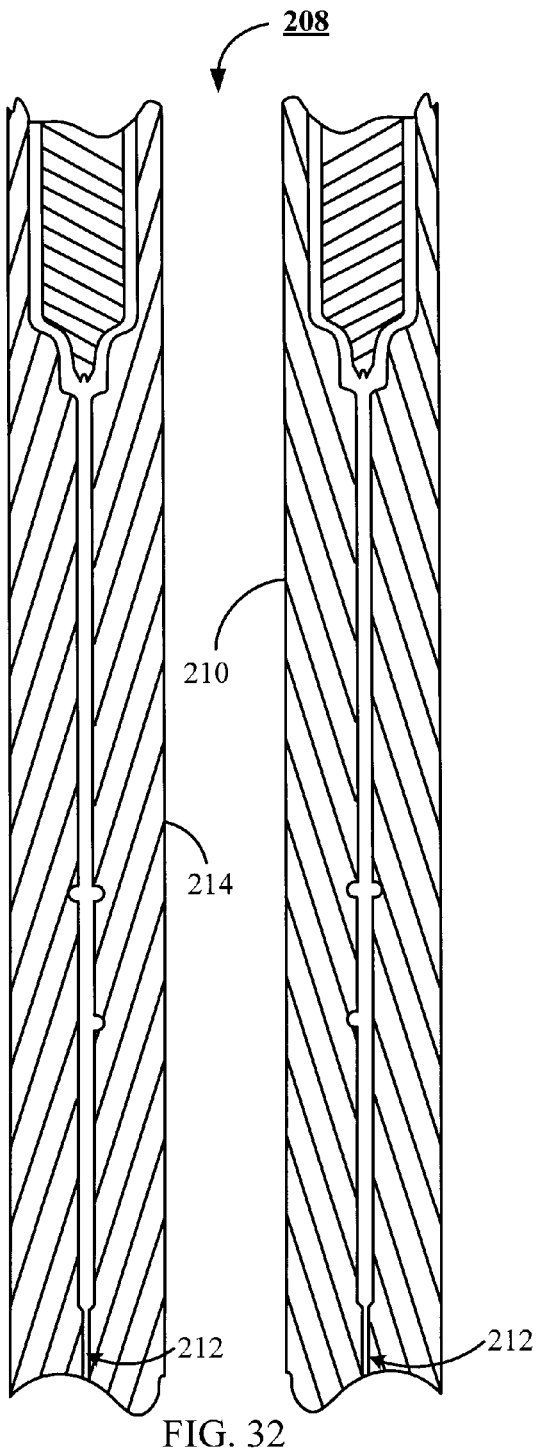
FIG. 32 reveals a view in elevation of an insert mold used in forming the medical procedures implement of FIG. 20.

FIG. 32 shows an insert mold 208 for use in producing the medical procedures implement 198. The insert mold preferably includes a first half 210, a needle confinement cavity 212 that is fully formed when a second half 214 is joined to the first half 210. When fully formed, the needle confinement cavity 212 constrains rotation of a hypodermic needle 188 (of FIG. 17) to assure the tip of the needle is held in a fixed position relative to the instrument carrier 182 (of FIG. 16).

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. A medical procedure kit comprising:
   a circular frame comprising a base and a patient attachment member, wherein the patient attachment member attaches the frame to a body of a patient via an adhesive;
   an instrument positioning assembly supported by said frame comprising an instrument guide and a position shuttle supported by the circular frame and communicating with a position adjustment member and a pitch adjustment member, wherein the position adjustment member controls the position of the position shuttle laterally relative to the base of the frame and a pitch adjustment member anchored by the position shuttle and configured to adjust a pitch angle of the instrument guide relative to the base of the circular frame; and
   an instrument advancing member configured to engage and advance the instrument positioning assembly towards the body of the patient along the pitch angle adjusted by the pitch adjustment member.

2. The medical procedure kit of claim 1, further comprising an instrument carrier configured to secures an instrument in a rotationally fixed position relative to said instrument positioning assembly.

3. The medical procedure kit of claim 1, in which said position shuttle provides a positioning aperture and a pitch adjustment aperture adjacent said positioning aperture, and in which said position adjustment member provides at least a threaded body for interaction with said positioning aperture, and wherein said pitch adjustment aperture cooperates with said pitch adjustment member to provide an angled alignment of said instrument guide relative to said body of said patient.

4. The medical procedure kit of claim 3, in which said angled alignment is selected by a rotation of said pitch adjustment member.

5. The medical procedure kit of claim 3, in which said position adjustment member further comprises a retention channel adjacent said threaded body, wherein said retention channel is confined by said frame, and wherein said threaded body cooperates with said positioning aperture to provide alignment of said instrument guide relative to said body of said patient.

6. The medical procedure kit of claim 1, in which said instrument guide comprises a first instrument guide body and a second instrument guide body, wherein said first instrument guide body provides an attachment element that interacts with a corresponding attachment element of said second instrument guide body.

7. The medical procedure kit of claim 6, in which said instrument carrier comprises an instrument orientation feature, and in which said first instrument guide body provides an instrument orientation channel configured for interaction with said instrument orientation feature.

8. The medical procedure kit of claim 1, in which said position shuttle provides a positioning aperture, and in which said pitch adjustment member includes at least a pair of end caps with a main body disposed there between, wherein said positioning aperture is configured to interact with either of said pair of end caps, and wherein said pitch adjustment member is confined by said position shuttle.

9. The medical procedure kit of claim 1, in which said circular frame provides a first shuttle slide aperture that accommodates a slide of said position shuttle and a second shuttle slide aperture that accommodates a second slide of said position shuttle, wherein a plurality of instrument alignment apertures are offset one from the other, and wherein rotation of said position adjustment member selectively positions said position shuttle along said shuttle slide apertures.

* * * * *